United States Patent [19]

Fujimura et al.

[11] Patent Number: 6,121,475
[45] Date of Patent: Sep. 19, 2000

[54] PREPARATION OF OPTICALLY ACTIVE β-HYDROXYESTER DERIVATIVES AND PLATINUM-CONTAINING CATALYST

[75] Inventors: Osamu Fujimura; Kikuo Ataka, both of Ube, Japan

[73] Assignee: Ube Industries, Ltd., Yamagushi, Japan

[21] Appl. No.: 09/397,812

[22] Filed: Sep. 17, 1999

[51] Int. Cl.[7] .................................. C07F 7/08; C07F 7/18
[52] U.S. Cl. ............................................................ 556/437
[58] Field of Search ............................................. 556/437

[56] References Cited

U.S. PATENT DOCUMENTS 5,354,879  10/1994  Konoike et al. ..................... 556/437 X
5,985,853  11/1999  Laugraud et al. ................... 556/437 X

*Primary Examiner*—Paul F. Shaver
*Attorney, Agent, or Firm*—Reed Smith Shaw & McClay, LLP

[57] ABSTRACT

In a process for preparing an optically active β-hydroxyester derivative by enantioselective aldol addition reaction between an aldehyde and a ketene silylacetal, the enantioselective aldol addition reaction is performed in the presence of an organic base and a platinum-containing catalyst composed of an optically active bisphosphine-platinum complex having two P—Pt bondings which are equivalent to each other, showing in its $^{31}$P NMR spectrum a single peak assigned to P—Pt bonding.

7 Claims, No Drawings

PREPARATION OF OPTICALLY ACTIVE β-HYDROXYESTER DERIVATIVES AND PLATINUM-CONTAINING CATALYST

FIELD OF THE INVENTION

The present invention relates to a process for preparing an optically active β-hydroxyester derivative by enantioselective aldol addition reaction between an aldehyde and a ketene silylacetal, using a new platinum-containing catalyst. The invention also resides in the new platinum-containing catalyst.

BACKGROUND OF THE INVENTION

The optically active β-hydroxyester derivatives are utilized in industry as intermediates for preparing pharmaceutically active compounds, agricultural chemicals, and other fine chemicals.

As a process for preparing the optically active β-hydroxyester derivative (which is an optically active β-hydroxyester protected by a silyl group at its hydroxyl group), Mukaiyama aldol reaction which comprises reacting an aldehyde and a ketene silyl acetal in the presence of an optically active Lewis acid catalyst is known. As the Lewis acid catalyst, various organometallic compounds such as those containing titanium, tin, boron or copper as their central metals are known. However, these organometallic metal compounds have certain drawbacks.

For instance, organometallic compounds other than organic copper compounds, such as organic titanium compounds, organic tin compounds, and organic boron compounds, are unstable in water. Therefore, the reaction should be performed in a non-aqueous phase. The reaction in a non-aqueous phase requires complicated procedures and therefore is disadvantageous in industry.

In the use of an organic copper compound, it is required to employ an aldehyde having a Lewis basic functional group for causing asymmetric induction. Such requirement to employ the specific aldehyde compound as the starting compound is disadvantageous from the viewpoint of industrial production. See J. Am. Chem. Soc., 118, 5814 (1996).

The organic titanium compound which gives a high enantiomer excess at a relatively small amount further has drawbacks in that the preparation of a ligand required for the asymmetric induction is not easy and requires carcinogenic β-aminonaphthalene as a starting compound. See J. Am. Chem. Soc., 116, 8837 (1994).

The organic tin compound is disadvantageous because it should be employed in a large amount in the reaction. See Tetrahedron, 49, 1761 (1993). Furthermore, the organic tin compounds are nowadays said to act as endocrine disruptors to give adverse effects to human bodies.

The organic boron compound is also disadvantageous because it should be employed in a large amount in the reaction. See Tetrahedron Lett., 33, 1729 (1992), and Bull. Chem. Soc. Jpn., 66, 3483 (1993).

SUMMARY OF THE INVENTION

It is an object of the invention to provide a new catalyst favorably employable in a process for preparing an optically active β-hydroxyester derivatives from an aldehyde and a ketene silyl acetal, which is stable in water, causes asymmetric induction even in the use of generally available aldehydes, is easily produced from generally available starting compounds by simple procedures, and gives the desired optically active β-hydroxyester derivatives (in which the hydroxyl group is protected by a silyl group) by the reaction in the presence of a small amount of the catalyst.

The present invention resides in an improved process for preparing an optically active β-hydroxyester derivative having the formula (1):

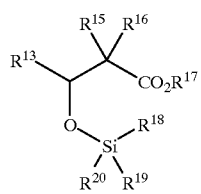

(1)

wherein $R^{13}$ stands for an alkenyl group, an alkadienyl group, an alkynyl group, an aryl group, or a group represented by $-CH_2R^{14}$ in which $R^{14}$ is an alkyl group, an alkenyl group, an alkadienyl group, an alkynyl group, an aryl group, an aralkyl group, an alkoxyalkyl group or an aryloxyalkyl group, in which any of $R^{13}$ and $^{14}$ may have one or more substituent groups, and each of $R^{15}$, $R^{16}$, $R^{18}$, $R^{19}$ and $R^{20}$ independently stands for a hydrogen atom, a halogen atom, an alkyl group, an aryl group, an aralkyl group, an alkoxy group, an alkoxyalkyl group, an aryloxy group, or an aryloxyalkyl group; and $R^{17}$ stands for an alkyl group, an aryl group, or aralkyl group; provided that two groups selected from the group consisting of $R^{15}$, $R^{16}$ and $R^{17}$ may form a ring in conjunction with the adjacent atom or atoms, by enantioselective aldol addition reaction between an aldehyde having the formula (2) and a ketene silylacetal having the formula (3):

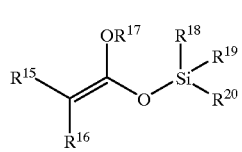

(3)

wherein each of $R^{13}$, $R^{15}$, $R^{16}$, $R^{17}$, $R^{18}$, $R^{19}$ and $R^{20}$ has the same meaning as above.

The improvement provided by the present invention comprises performing the enantioselective aldol addition reaction in the presence of an organic base and a platinum-containing catalyst comprising an optically active bisphosphine-platinum complex having two P—Pt bondings which are equivalent to each other.

The silyl group which protects the hydroxyl group of the optically active β-hydroxyester derivative of the above-illustrated formula (I) can be readily removed by a method described in "Protective Groups in Organic Synthesis" 1st edition, p39–50.

The invention further resides in the platinum-containing catalyst comprising an optically active bisphosphine-platinum complex having two P—Pt bondings which are equivalent to each other.

DETAILED DESCRIPTION OF THE INVENTION

The process for preparing the optically active β-hydroxyester derivative of the formula (I) is illustrated as follows.

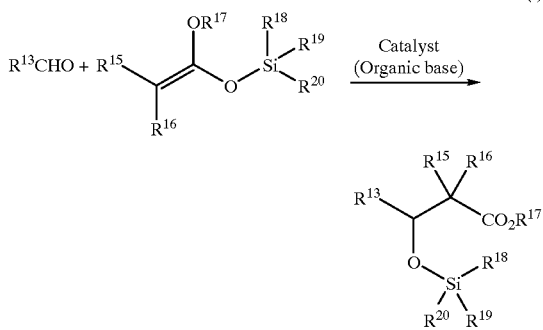

The platinum-containing catalyst of the invention preferably shows in its $^{31}$P NMR spectrum a single peak assigned to P—Pt bonding and preferably shows one of the following combinations (1) to (3):

(1) a chemical shift in the range of −3.0 ppm to 7.0 ppm, and a phosphorus—platinum coupling constant in the range of 3,400 Hz to 4,200 Hz;

(2) a chemical shift in the range of 40.0 ppm to 50.0 ppm, and a phosphorus—platinum coupling constant in the range of 2,700 Hz to 3,300 Hz; and (3) a chemical shift in the range of 55.0 ppm to 65.0 ppm, and a phosphorus—platinum coupling constant in the range of 3,200 Hz to 3,800 Hz.

The platinum-containing catalyst of the invention is preferably produced by treating an optically active bisphosphine-aryloxyacyl platinum(II) complex having the formula (4):

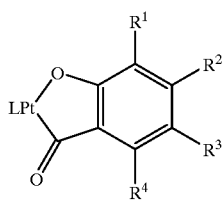

wherein each of $R^1$, $R^2$, $R^3$ and $R^4$ independently represents a hydrogen atom, a halogen atom, an alkyl group, an alkenyl group, an aryl group, an aralkyl group, an alkoxy group, an aryloxy group, a nitro group, a cyano group or a dialkylamino group, provided that two groups selected from the group consisting of $R^1$, $R^2$, $R^3$ and $R^4$ may form a ring in conjunction with the adjacent atoms; and L represents an optically active bisphosphine, with a non-coordinating or weakly coordinating super-strong acid in an oxygen-containing gas.

The optically active bisphosphine-aryloxyacyl platinum (II) complex of the formula (4) can be produced by reacting potassium tetrachloroplatinate with a salicylaldehyde compound and then reacting the resulting compound with an optically active divalent phosphine corresponding to "L", in the process described in Organometallics, 13, 3442 (1994).

Examples of the halogen atoms which may be present in the formula (4) include atoms of fluorine, chlorine, bromine, and iodine. Examples of the alkyl groups include alkyl groups having 1 to 20 carbon atoms, preferably 1 to 12 carbon atoms, such as methyl, ethyl, propyl, butyl, pentyl, hexyl, heptyl, octyl, nonyl, decyl and dodecyl. Examples of the alkenyl groups include alkenyl groups having 2 to 20 carbon atoms, preferably 2 to 12 carbon atoms, such as vinyl, propenyl, butenyl, pentenyl, hexenyl, heptenyl, octenyl, nonenyl, decenyl and dodecenyl. Examples of the aryl groups include aryl groups having 6 to 20 carbon atoms, preferably 6 to 12 carbon atoms, such as phenyl, tolyl, xylyl, naphthyl and dimethylnaphthyl. Examples of the alkoxy groups include alkoxy groups having 1 to 10 carbon atoms, such as methoxy, ethoxy, propoxy, butoxy and pentoxy. Examples of the aryloxy groups include aryloxy groups having 6 to 14 carbon atoms, such as phenoxy, tolyloxy, xyloloxy and naphthoxy. Examples of the dialkylamino groups include dialkylamino groups having 2 to 10 carbon atoms, such as dimethylamino and diethylamino. Examples of the aralkyl groups include aralkyl groups having 7 to 21 carbon atoms, preferably 7 to 13 carbon atoms, such as benzyl, phenylethyl, tolylmethyl, xylylmethyl and naphthylmethyl.

The alkyl groups, alkenyl groups, aryl groups, aralkyl groups, alkoxy groups, aryloxy groups and dialkylamino groups can be in the form of their any isomers, such as n-, iso-, sec-, tert-, o-, m-, α-, and β-.

When $R^1$ through $R^4$ are the above-mentioned alkyl, alkenyl, aryl, aralkyl, alkoxy, aryloxy, or dialkyl amino, any adjacent combinations of $R^1$ through $R^4$ (e.g., $R^1$ and $R^2$, $R^2$ and $R^3$, $R^3$ and $R^4$, and/or $R^3$ and $R^4$) can be combined to form a ring such as an aromatic ring (e.g., benzene ring) or a cycloalkanoic acid having 4 to 8 carbon atoms (e.g, cyclopentane or cyclohexane). The ring may contain a hetero atom such as an oxygen atom as a ring member.

The optically active bisphosphine (L) has one of the following formulas (2-a), (2-b), (3-a), (3-b), (4-a), (4-b), (5-a), and (5-b):

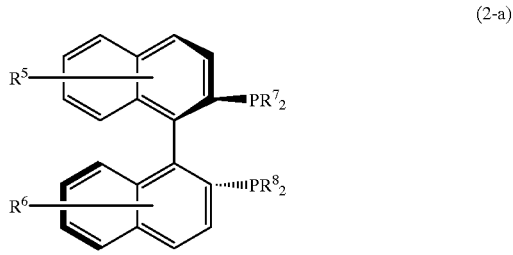

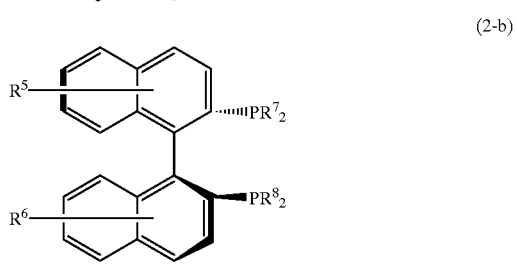

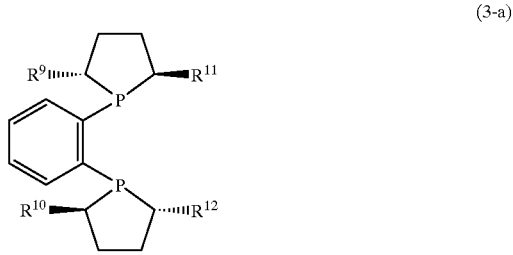

-continued (3-b)

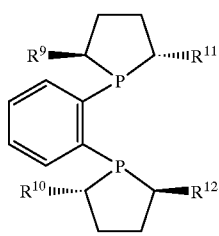

(4-a)

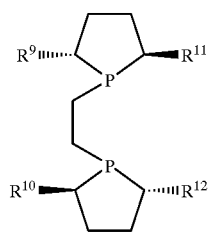

(4-b)

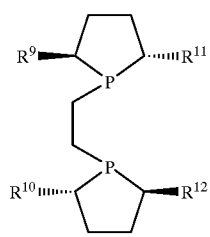

(5-a)

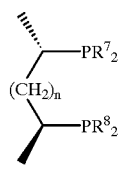

(5-b)

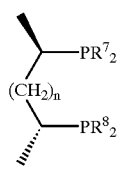

wherein each of $R^7$, $R^8$, $R^9$, $R^{10}$, $R^{11}$ and $R^{12}$ independently is an alkyl group, a cycloalkyl group, an aryl group, or an aralkyl group; each of $R^5$ and $R^6$ is a substituent group placed on the naphthalene ring, which independently is a halogen atom, an alkyl group, an aryl group or an aralkyl group; and n is an integer of 0 to 10.

In the above-illustrated formulas of the optically active bisphosphine (L), alkyl groups and aryl groups for the groups of $R^5$, $R^6$, $R^7$, $R^8$, $R^9$, $R^{10}$, $R^{11}$ and $R^{12}$ can be alkyl groups and aryl groups described hereinbefore for the alkyl groups and aryl groups of $R^1$ to $R^4$. The aforementioned halogen atoms can be also mentioned. Examples of the cycloalkyl groups for $R^7$, $R^8$, $R^9$, $R^{10}$, $R^{11}$ and $R^{12}$ include cycloalkyl groups having 5 to 7 carbon atoms, such as cyclopentyl and cyclohexyl. In the preferred compounds, each of $R^5$ and $R^6$ is a halogen atom, an alkyl group, or an aryl group, and the naphthalene ring has one or two groups of $R^5$ and $R^6$.

The preferred optically active bisphosphine (L) are as follows:

1) BINAP represented by the formula (2-a) or (2-b) in which each of $R^7$ and $R^8$ is phenyl, and each of $R^5$ and $R^6$ is hydrogen;
2) Tol-BINAP represented by the formula (2-a) or (2-b) in which each of $R^7$ and $R^8$ is p-tolyl, and each of $R^5$ and $R^6$ is hydrogen;
3) Me-DUPHOS represented by the formula (3-a) or (3-b) in which each of $R^9$, $R^{10}$, $R^{11}$ and $R^{12}$ is methyl;
4) Et-DUPHOS represented by the formula (3-a) or (3-b) in which each of $R^9$, $R^{10}$, $R^{11}$ and $R^{12}$ is ethyl;
5) CHIRAPHOS represented by the formula (5-a) or (5-b) in which each of $R^7$ and $R^8$ is phenyl, and n is 0; and
6) BDPP represented by the formula (5-a) or (5-b) in which each of $R^7$ and $R^8$ is phenyl, and n is 1.

Examples of the optically active bisphosphine-aryloxyacyl platinum(II) complexs of the formula (4) are as follows:

1) Compound A: each of $R^1$ and $R^3$ is t-butyl, each of $R^2$ and $R^4$ is hydrogen, and L is BINAP;
2) Compound B: each of $R^1$ through $R^4$ is hydrogen, and L is BINAP;
3) Compound C: each of $R^1$ and $R^3$ is t-butyl, each of $R^2$ and $R^4$ is hydrogen, and L is Tol-BINAP;
4) Compound D: each of $R^1$ through $R^4$ is hydrogen, and L is Me-DUPHOS; and
5) Compound E: each of $R^1$ through $R^4$ is hydrogen, and L is CHIRAPHOS.

The above-described Compounds A, B, C, D and E are illustrated below.

(A)

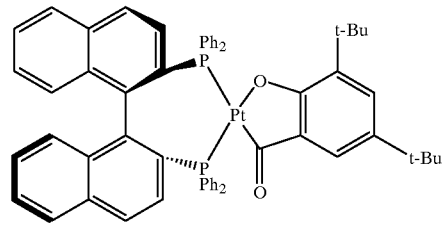

(B)

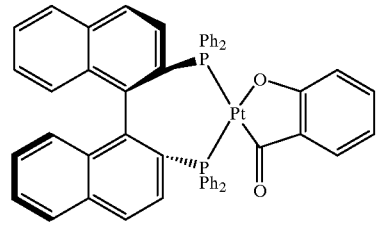

(C)

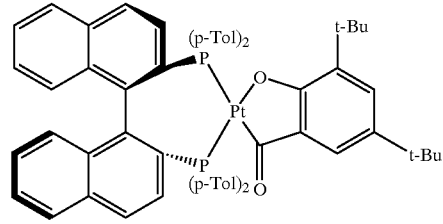

-continued

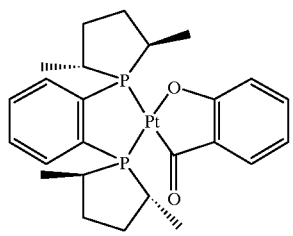

(D)

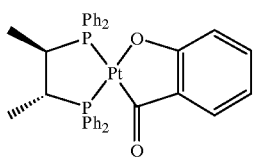

(E)

The platinum-containing catalyst of the invention can be produced by treating the aforementioned optically active bisphosphine-aryloxyacyl platinum(II) complex of the formula (4) with a non-coordinating or weakly coordinating super-strong acid (or superacid) in an oxygen ($O_2$)-containing gas. There is no specific limitation with respect to the oxygen content in the gas. The gas can be 100% oxygen gas. Generally, the oxygen content is in the range of 0.01 to 100 vol. %, preferably 1 to 100 vol. %, more preferably 15 to 25 vol. %. The temperature for the treatment generally is in the range of −78° C. to 140° C., preferably 0 to 30° C. There is no specific limitation with respect to pressure for the treatment. Generally, the treatment is performed in an oxygen gas diluted with an inert gas such as nitrogen gas, in air, or in a 100% oxygen gas. The treatment is generally performed in a solvent.

Examples of the super-strong acid include trifluoromethanesulfonic acid, tetrafluoroboric acid, hexafluorophosphoric acid, hexafluoroantimonic, acid and perchloric acid. Most preferred is trifluoromethanesulfonic acid. The super-strong acid can be employed in an amount of 1 to 20 equivalents, preferably 1 to 4 equivalents, based on one equivalent amount of the optically active bisphosphine-aryloxy platinum(II) of the formula (4).

The treatment of the optically active bisphosphine-aryloxy platinum(II) in an oxygen-containing gas is preferably carried out in the presence of water, so as to accelerate the treatment. In the treatment, water is preferably employed in an amount of 1 to 20 equivalents, preferably 2 to 4 equivalents, based on one equivalent amount of the optically active bisphosphine-aryloxy platinum(II). The water can be added to the solvent for the treatment. The addition of water to the solvent can be made before or during the treating procedure.

Examples of the solvents employable in the treating procedure include halogenated aliphatic hydrocarbons such as dichloromethane and dichloroethane, aromatic hydrocarbons such as benzene, toluene and xylene, ethers such as diethyl ether, diisopropyl ether and tetrahydrofuran, amides such as dimethylformamide, sulfoxides such as dimethylsulfoxide, and nitriles such as acetonitrile. Most preferred is a halogenated aliphatic hydrocarbon. The solvent can be employed in an amount of 10 to 1,000 mL, preferably 50 to 500 mL, based on 1 mmol. of the optically active bisphosphine-aryloxy platinum(II).

Thus obtained platinum-containing catalyst shows in its $^{31}P$ NMR spectrum a single peak assigned to P—Pt bonding, while the untreated optically active bisphosphine-aryloxy platinum(II) shows in its $^{31}P$ NMR spectrum two peaks which are assigned to two P—Pt bonding having different bonding energy.

Accordingly, the platinum-containing catalyst of the invention is understood to have the formula (5):

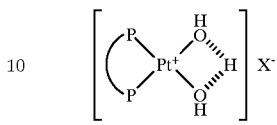

(5)

wherein the curve having P on its either end represents an optically active bisphosphine, and $X^-$ is an anion.

Examples of the platinum-containing catalysts of the invention are those in which the $^-P$ NMR spectrum shows one of the following combinations (1) to (3):

(1) a chemical shift in the range of −3.0 ppm to 7.0 ppm, and a phosphorus—platinum coupling constant in the range of 3,400 Hz to 4,200 Hz, which is produced using an optically active bisphosphine-aryloxyacyl platinum (II) complex of the formula (4) in which L is BINAP or Tol-BINAP;

(2) a chemical shift in the range of 40.0 ppm to 50.0 ppm, and a phosphorus—platinum coupling constant in the range of 2,700 Hz to 3,300 Hz, which is produced using an optically active bisphosphine-aryloxyacyl platinum (II) complex of the formula (4) in which L is CHIRAPHOS; and (3) a chemical shift in the range of 55.0 ppm to 65.0 ppm, and a phosphorus—platinum coupling constant in the range of 3,200 Hz to 3,800 Hz, which is produced using an optically active bisphosphine-aryloxyacyl platinum (II) complex of the formula (4) in which L is DUPHOS.

In the process of the invention for preparing an optically active β-hydroxyester derivative, an aldehyde having the aforementioned formula (2) is employed. In the formula (2), the aryl groups for $R^{13}$ and $R^{14}$ can be aryl groups having 6 to 20 carbon atoms, preferably 6 to 12 carbon atoms, such as phenyl, tolyl, xylyl and naphthyl; the aralkyl groups for $R^{13}$ and $R^{14}$ can be aralkyl groups having 7 to 20 carbon atoms, preferably 7 to 12 carbon atoms, such as benzyl, phenethyl, tolylmethyl, and naphthylmethyl; the alkenyl groups for $R^{13}$ and $R^{14}$ can be alkenyl groups having 2 to 20 carbon atoms, such as vinyl, propenyl, butenyl, pentenyl and decenyl; the alkadienyl groups for $R^{13}$ and $R^{14}$ can be alkadienyl groups having 4 to 20 carbon atoms, preferably 4 to 10, such as butadienyl, pentadienyl, hexadienyl, heptadienyl, octadienyl, nonadienyl and decadienyl, in which two double bonds may be conjugated; the alkynyl groups for $R^{13}$ and $R^{14}$ can be alkynyl groups having 2 to 20 carbon atoms, such as ethynyl, propynyl, butynyl, pentynyl, hexynyl, heptynyl, octynyl, nonynyl and decynyl; the alkyl groups for $R^{14}$ can be alkyl groups having 1 to 20 carbon atoms, such as methyl, ethyl, propyl, butyl, pentyl, hexyl, heptyl, octyl, nonyl and decyl. The aryl, aralkyl, alkenyl, alkadienyl, alkynyl and alkyl groups man be in the form of various isomers. Each of the groups can have one or more substituents.

Examples of the substituents which can be attached to $R^{13}$ and $R^{14}$ include alkyl, alkenyl, aryl, aralkyl, alkoxy, aryloxy, nitro, cyano, dialkylamino, and halogen. Examples of these substituents are those described hereinbefore for $R^1$ to $R^4$. As the substituents which can be attached to $R^{13}$ and $R^{14}$, the following groups can be also mentioned: alkyl- or arylthio groups having 1 to 6 carbon atoms, such as methylthio, ethylthio, hexylthio and phenylthio, cycloalkyl groups having 3 to 7 carbon atoms, such as cyclopropyl, cyclopentyl, cyclohexyl and cycloheptyl, alkoxycarbonyl groups having 2 to 10 carbon atoms, such as methoxycarbonyl, ethoxycarbonyl and propoxycarbonyl, aryloxy groups having 6 to 10 carbon atoms, such as phenoxy and tolyloxy, and a hydroxyl group. These substituents can be in the form of various isomers.

Examples of the aldehyde compounds of the formula (2) include benzaldehyde, tolylaldehyde, xylylaldehyde, anisaldehyde, cinnamaldehyde, 2-methoxycinnamaldehyde, 4-dimethylaminocinnamaldehyde, 4-nitrocinnamaldehyde, 4-chlorocinnamaldehyde, naphthylaldehyde, acrolein, metacrolein, crotonaldehyde, 2-hexenal, 2-heptenal, 2-decenal, 3-(3-nitrophenyl)propenal, 2,4-hexadienal, 2,4-heptadienal, 2,4-octadienal, propargylaldehyde, acetaldehyde, propionaldehyde, butanal, hexanal, heptanal, octanal, nonanal, dodecanal, hydrocinnamaldehyde, anisylpropionaldehyde, 3-cyanopropionaldehyde, 3-cyclohexylpropionaldehyde, methyl 3-formylpropionate, 3-phenylbutanal, 3-methylbutanal, 3,3-dimethylbutanal, 3-methylthiobutanal, 3-hydroxybutanal, 5-(p-chlorophenoxy)-1-pentanal, 6-bromo-4-methyhexanal, 7-bromoheptanal, 2-phenylacetaldehyde, p-tolylacetaldehyde, 4-pentenal, 3-hexenal, 7-decenal, citronellal, 5,7-dodecadienal, 7,11-hexadienal, and 3-pentyn-1-al.

In the formula (3) of the ketene silyl acetals, examples of halogen, alkyl, aryl, aralkyl, alkoxy, aryloxy for $R^{15}$, $R^{16}$, $R^{18}$, $R^{19}$, and $R^{20}$ and alkyl, aryl and aralkyl for $R^{17}$ are those described hereinbefore for $R^1$ to $R^4$. The groups of $R^{15}$, $R^{16}$, $R^{17}$, $R^{18}$, $R^{19}$ and $R^{20}$ may have one or more substituents such as those described above for $R^{13}$ and $R_{14}$.

Examples of the ketene silyl acetals include methyl (trimethylsilyl)ketene acetal, ethyl(trimethylsilyl)ketene acetal, t-butyl(trimethylsilyl)ketene acetal, phenyl (trimethylsilyl)ketene acetal, methyl(trimethylsilyl) methylketene acetal, ethyl(trimethylsilyl)methylketene acetal, t-butyl(trimethylsilyl)methylketene acetal, methyl (trimethylsilyl)dimethylketene acetal, ethyl(trimethylsilyl) dimethylketene acetal, t-butyl(trimethylsilyl) dimethylketene acetal, methyl(trimethylsilyl)dichloroketene acetal, ethyl(trimethylsilyl)dichloroketene acetal, 1-methoxy-1-trimethylsilyloxy-methylenecyclohexane, 1-methoxy-1-trimethylsilyloxy-2-methyl-1,3-butadiene.

A representative example of the organic base employed in the preparation of the optically active β-hydroxyester derivative of the formula (1) is pyridine which may have one or more substituents. Examples of the substituents include alkyl, alkenyl, aryl, aralkyl, alkoxy, aryloxy, dialkylamino, nitro, and halogen. If two or more substituents are present, two adjacent substituents may be combined to form a ring.

Examples of the above-mentioned alkyl, alkenyl, aryl, aralkyl, alkoxy, aryloxy, dialkylamino, nitro, and halogen can be those described hereinbefore for $R^1$ to $R^4$. These substituents can be in the form of various isomers, and further have one or more substituents such as those for $R^{13}$ and $R^{14}$.

Examples of unsubstituted or substituted pyridines include pyridine, picoline, ethylpyridine, propylpyridine, butylpyridine, lutidine, collidine, chloropyridine, phenylpyridine, vinylpyridine, benzylpyridine, pyrrolidinopyridine, quinoline, and isoquinoline. These compounds can be in the form of various isomers.

In the process of the invention for preparing an optically active β-hydroxyester derivative of the formula (1), the platinum-containing catalyst can be employed without separating it from the reaction mixture which is obtained by treating the optically active bisphosphine-aryloxyacyl platinum(II) complex with a super-strong acid in an oxygen-containing gas. In more detail, the reaction mixture per se (namely, not converted to a nonaqueous reaction mixture) can be employed for conducting the reaction between the aforementioned aldehyde and ketene silyl acetal in the presence of an organic base to produce the desired β-hydroxyester derivative of the formula (1).

In the reaction, the aldehyde can be employed in an amount of up to approximately 1,000 equivalents, preferably 2 to 1,000 equivalents, more preferably 20 to 1,000 equivalents, based on one equivalent amount of the starting optically active bisphosphine-aryloxyacyl platinum (II) complex. The organic base can be employed singly or in combination in an amount of 0.1 to 10 equivalents, preferably 0.5 to 2 equivalents, based on one equivalent amount of the superstrong acid. The ketene silyl acetal can be employed in an amount of 1 to 100 equivalents, preferably 1 to 2 equivalents, based on one equivalent amount of the aldehyde. The reaction can be performed at a temperature of −78° C. to 0° C., preferably −75° C. to −20° C. There is no limitation with respect to the reaction pressure. The produced β-hydroxyester derivative can be isolated from the reaction mixture by conventional procedures such as extraction and column chromatography.

The present invention is further described by the following examples and comparison examples.

EXAMPLE 1

(1) Preparation of Optically Active Bisphosphine-Aryloxyacyl Platinum(II) Complex (A)

In a Schlenk tube (100 mL volume) were placed potassium tetrachloro platinate (1.6 mmol.), sodium carbonate (4.8 mmol.), 3,5-di-t-butyl-2-hydroxybenzaldehyde (1.6 mmol.) and dimethylsulfoxide (25 mL). They were stirred at 140° C. for 40 minutes. The mixture was then heated to 100° C., and (R)-BINAP (1.6 mmol.) was added. The reaction mixture was then cooled to 60° C. and placed under reduced pressure to distill dimethylsulfoxide off. The residue was extracted with methylene chloride and recrystallized from ethanol to obtain 1.4 g of an optically active bisphosphine-aryloxyacyl platinum(II) complex represented by the aforementioned (A). Yield: 83%. The analytical data are given below.

1) $^1$H-NMR (400 MHz, CDCl$_3$) δ: 7.91–7.86 (m, 4H), 7.55–6.98 (m, 22H), 6.75–6.72 (m, 4H), 6.60–6.57 (m, 4H), 1.20 (s, 9H), 1.03 (s, 9H).

2) $^{31}$P{$^1$H}-NMR (160 MHZ, CDCl$_3$) δ: 23.7 (d, $J_{P-P}$=10.7, $J_{Pt-P}$=1512, trans to C), 20.4 (d, $J_{P-P}$=10.7, $J_{Pt-P}$=4474, trans to O).

3) $[\alpha]_D^{25}$=+582° (c=0.44, CH$_2$Cl$_2$).

4) Elemental analysis

Calculated C: 67.48, H: 4.99

Found C: 66.38, H: 4.94.

(2) Preparation of Platinum-Containing Catalyst

Under atmospheric conditions, 0.025 mmol. of the optically active bisphosphine-aryloxyacyl platinum(II) complex obtained above was introduced into a Schlenk tube (25 mL volume). Further, 2.5 mL of a solvent (methylene chloride) containing 0.05 mmol. of water (water content: 300 ppm) and subsequently trifluoromethanesulfonic acid (0.025 mmol) were added. The mixture was stirred at room temperature to perform treatment using the super-strong acid for 15 minutes to prepare a solution of the desired platinum-containing catalyst.

(3) Preparation of β-Hydroxyester Derivative

Thus prepared solution of the platinum-containing catalyst was chilled to −78° C., and to this chilled solution was added 2,6-lutidine (0.025 mmol.). To the mixture were dropwise added successively hydrocinnamaldehyde (0.5 mmol.) and methyltrimethylsilyldimethylketene acetal (0.7 mmol.). The gaseous condition was made to an argon gas condition, the mixture was subjected to reaction at −25° C. for 168 hours. After the reaction was complete, the reaction mixture was washed with water, treated with hydrochloric acid, and extracted with methylene chloride. The extract was dried and subjected to column chromatography to give a colorless oily product (methyl 2,2-dimethyl-5-phenyl-3-trimethylsiloxypentanoate: 145 mg). Yield: 94%. The analytical data are given below.

1) IR(neat): 2955, 1729, 1251, 1132, 1101, 840, 751, 699 ($cm^{-1}$).

2) $^1$H-NMR (270 MHz, $C_6D_6$) δ: 7.18–7.03 (m, 5H), 4.06 (dd, J=8.1, 2.9, 1H), 3.29 (s, 3H), 2.88–2.78 (m, 1H), 2.55–2.37 (m, 1H), 1.75–1.60 (m, 2H), 1.20 (s, 3H), 1.06 (s, 3H), 0.13 (s, 9H).

3) $^{13}$C-NMR (67.5 MHZ, $C_6D_6$) δ: 177.0, 142.5, 128.7, 128.6, 126.2, 77.9, 51.2, 48.4, 35.4, 33.9, 21.3, 20.9, 0.9.

4) Mass spectrum (CI) m/z (relative intensity): 309 ($MH^+$, 40), 219 (98), 159 (45), 117 (100), 91 (96), 73 (70).

The trimethylsilyl group of the above-obtained product was removed in a tetrabutylammonium fluoride/tetrahydrofuran solution to give methyl 3-hydroxy-2,3-dimethyl-5-phenylpetanoate. The enantiomer excess determined by high speed liquid chromatography was 95% e.e. The chromatographic conditions are set forth below:

Column: ChiralPak-AD (available from Daicel Corporation Ltd.)

Eluent: hexane/ethanol/trifluoroacetic acid=97.5/2.5/0.1 (vol.); 0.8 mL/min.

Column temp.: 30° C.

Detection: UV (220 nm)

Separately, under atmospheric conditions, 0.025 mmol. of the optically active bisphosphine-aryloxyacyl platinum(II) complex (A) was mixed with 1 mL of a solvent (methylene chloride-$d_2$) containing 0.05 mmol. of water in an NMR sample tube. Still under atmospheric conditions, trifluoromethanesulfonic acid (0.025 mmol) was added for performing the treatment with a super-strong acid at room temperature.

The reaction mixture was subjected to $^{31}$P-NMR analysis. The obtained $^{31}$P-NMR spectrum showed one signal of chemical shift(δ)=3.3 ppm (singlet) and a phosphorus-platinum coupling constant ($J_{Pt-P}$) of 3674 Hz.

EXAMPLE 2

(1) Preparation of Platinum-Containing Catalyst

The treatment of the optically active bisphosphine-aryloxyacyl platinum(II) complex (A) produced in Example 1 by a super-strong acid was performed in the manner described in Example 1, except for replacing the solvent with dry methylene chloride (2.5 mL). The procedure in the NMR sample tube was repeated in the same manner as described in Example 1 to give a product which was the same as that of Example 1.

(2) Preparation of β-Hydroxyester Derivative

The reaction of Example 1 was repeated except for using the reaction mixture obtained above and changing the reaction time to 141 hours, to give 152 mg of a colorless oily product (methyl 2,2-dimethyl-5-phenyl-3-trimethylsiloxypentanoate). Yield: 99%. The enantiomer excess determined in the same manner as in Example 1 was 77% e.e.

COMPARISON EXAMPLE 1

(1) Preparation of Platinum-Containing Catalyst

The treatment of the optically active bisphosphine-aryloxyacyl platinum(II) complex (A) produced in Example 1 by a super-strong acid was performed in the manner described in Example 1, except for replacing the solvent with dry methylene chloride (2.5 mL) and changing the reaction atmosphere to an oxygen-free atmosphere (i.e. in a nitrogen gas). The procedure in the NMR sample tube was repeated in the same manner as described in Example 1 to give no product similar to that of Example 1.

(2) Preparation of β-Hydroxyester Derivative

The reaction of Example 1 was repeated except for using the reaction mixture obtained above and changing the reaction time to 138 hours, to give 102 mg of a colorless oily product (methyl 2,2-dimethyl-5-phenyl-3-trimethylsiloxypentanoate). Yield: 68%. The enantiomer excess determined in the same manner as in Example 1 was 16% e.e.

EXAMPLE 3

Preparation of β-Hydroxyester Derivative

The reaction of Example 1 was repeated using the platinum-containing catalyst solution obtained in Example 1, except for replacing the aldehyde with 3-methylbutanal (0.5 mmol.) and changing the reaction time to 140 hours, to give 120 mg of a colorless oily product (methyl 2,2,5-trimethyl-3-trimethylsiloxyhexanoate). Yield: 92%. The enantiomer excess determined in the same manner as in Example 1 was 91% e.e. The analytical data are given below.

1) IR(neat): 2957, 1742, 1469, 1251, 1132, 1096, 1032, 911, 841 ($cm^{-1}$).

2) $^1$H-NMR (400 MHz, $C_6D_6$) δ: 4.13 (dd, J=9.8, 2.0, 1H), 3.36 (s, 3H), 1.79–1.72 (m, 1H), 1.54–1.48 (m, 1H), 1.26 (s, 3H), 1.14 (s, 3H), 1.08–1.01 (m, 1H), 0.89 (d, J=6.8, 6H), 0.15 (s, 9H).

3) $^{13}$C-NMR (100 MHZ, $C_6D_6$) δ: 177.0, 76.0, 51.2, 48.4, 42.7, 24.8, 24.3, 21.5, 21.4, 20.5, 0.9.

4) Mass spectrum (CI) m/z (relative intensity): 261 ($MH^+$, 20), 245 (10), 171 (100), 139 (10), 111 (12).

EXAMPLE 4

Preparation of β-Hydroxyester Derivative

The reaction of Example 1 was repeated using the platinum-containing catalyst solution obtained in Example 1, except for replacing the aldehyde with 3,3-dimethylbutanal (0.5 mmol.) and changing the reaction time to 171 hours, to give 132 mg of a colorless oily product (methyl 2,2,5,5-tetramethyl-3-trimethylsiloxyhexanoate). Yield: 96%. The enantiomer excess determined in the same manner as in Example 1 was 86% e.e. The analytical data are given below.

1) IR(neat): 2955, 1741, 1262, 1252, 1131, 1098, 841 ($cm^{-1}$).

2) $^1$H-NMR (400 MHz, $C_6D_6$) δ: 4.26 (dd, J=7.3, 1.5, 1H), 3.35 (s, 3H), 1.46 (dd, J=14.7, 7.3, 1H), 1.33 (dd, J=14.7, 1.5, 1H), 1.24 (s, 3H), 1.10 (s, 3H), 0.93 (s, 9H), 0.19 (s, 9H).

3) $^{13}$C-NMR (100 MHZ, $C_6D_6$) δ: 177.0, 75.2, 51.2, 49.4, 47.7, 30.4, 30.2, 21.1, 21.0, 1.5.

4) Mass spectrum (CI) m/z (relative intensity): 275 ($MH^+$, 9), 259 (20), 185 (100), 117 (25), 73 (25).

EXAMPLE 5

Preparation of β-Hydroxyester Derivative

The reaction of Example 1 was repeated using the platinum-containing catalyst solution obtained in Example 1, except for replacing the aldehyde with benzaldehyde (0.5 mmol.) and changing the reaction time to 20.5 hours, to give 138 mg of a colorless oily product (methyl 2,2-dimethyl-3-phenyl-3-trimethylsiloxyhexanoate). Yield: 99%. The analytical data are given below.

1) IR(neat): 2954, 1743, 1727, 1252, 1133, 1094, 1068, 881, 843 (cm$^{-1}$).

2) $^1$H-NMR (270 MHz, C$_6$D$_6$) δ: 7.28–7.27 (m, 2H), 7.15–7.05 (m, 3H), 5.12 (s, 1H), 3.39 (s, 3H), 1.30 (s, 3H), 1.03 (s, 3H), 0.00 (s, 9H).

3) $^{13}$C-NMR (67.5 MHZ, C$_6$D$_6$) δ: 176.6, 141.3, 128.2, 127.8, 127.6, 79.7, 51.3, 49.3, 22.0, 19.5, 0.0.

4) Mass spectrum (CI) m/z (relative intensity): 281 (MH$^+$, 5), 265 (10), 191 (100), 73 (90).

The enantiomer excess determined in the same manner as in Example 1 except for replacing the eluent and flow rate to hexane/ethanol/trifluoroacetic acid=100/10/0.1, vol., 0.7 mL/min. was 59% e.e.

COMPARISON EXAMPLE 2
Preparation of β-Hydroxyester Derivative

The reaction of Example 1 was repeated using the platinum-containing catalyst solution obtained in Comparison Example 1, except for replacing the aldehyde with benzaldehyde (0.5 mmol.) and changing the reaction time to 16 hours, to give 138 mg of a colorless oily product (methyl 2,2-dimethyl-3-phenyl-3-trimethylsiloxyhexanoate). Yield: 99%. The enantiomer excess determined in the same manner as in Example 5 was 0% e.e.

EXAMPLE 6
Preparation of β-Hydroxyester Derivative

The reaction of Example 1 was repeated using the platinum-containing catalyst solution obtained in Example 1, except for replacing the aldehyde with trans-cinnumaldehyde (0.5 mmol.) and changing the reaction time to 144 hours, to give 276 mg of a colorless oily product (methyl (E)-2,2-dimethyl-5-phenyl-3-trimethylsiloxypentencate). Yield: 90%. The enantiomer excess determined in the same manner as in Example 5 was 46% e.e. The analytical data are given below.

1) IR(neat): 2954, 1740, 1251, 1135, 1066, 892, 877, 742, 745, 694 (cm$^{-1}$).

2) $^1$H-NMR (400 MHz, C$_6$D$_6$) δ: 7.24–7.01 (m, 5H), 6.51 (d, J=16.0, 1H), 6.22 (dd, J=16.0, 7.3, 1H), 4.63 (d, J=7.3, 1H), 3.39 (s, 3H), 1.34 (s, 3H), 1.16 (s, 3H), 0.13 (s, 9H).

3) $^{13}$C-NMR (100 MHZ, C$_6$D$_6$) δ: 176.5, 137.2, 132.6, 128.2, 128.1, 126.8, 110.6, 79.1, 51.3, 48.7, 21.6, 20.1, 0.4.

4) Mass spectrum (CI) m/z (relative intensity): 307 (MH$^+$, 1), 205 (100), 157 (46), 73 (55).

EXAMPLE 7
(1) Preparation of Platinum-Containing Catalyst

The treatment of the optically active bisphosphine-aryloxyacyl platinum(II) complex (A) produced in Example 1 by a super-strong acid was performed in the manner described in Example 1, except for replacing the solvent with dry methylene chloride (2.5 mL). The procedure in the NMR sample tube was repeated in the same manner as described in Example 1 to give a product which was the same as that of Example 1.

(2) Preparation of β-Hydroxyester Derivative

The reaction of Example 5 was repeated except for using the reaction mixture obtained above and changing the reaction time to 19 hours, to give 138 mg of a colorless oily product (methyl 2,2-dimethyl-3-phenyl-3-trimethylsiloxypropanoate). Yield: 99%. The enantiomer excess determined in the same manner as in Example 5 was 35% e.e.

EXAMPLE 8
(1) Preparation of Optically Active Bisphosphine-Aryloxyacyl Platinum(II) Complex (B)

The procedure of Example 1 was repeated except for replacing the 3,5-di-t-butyl-2-hydroxybenzaldehyde with salicylaldehyde (1.6 mmol.), to give 1.35 g of the aforementioned optically active bisphosphine-aryloxyacyl platinum(II) complex (B). Yield: 90%. The analytical data are given below.

1) $^1$H-NMR (400 MHz, CDCl$_3$) δ: 8.07–7.97 (m, 4H), 7.53–7.25 (m, 17H), 7.13–6.98 (m, 5H), 6.79–6.57 (m, 9H), 6.36 (dd, J=7.3, 7.3, 1H).

2) $^{31}$P{$^1$H}-NMR (160 MHZ, CDCl$_3$) δ: 24.4 (d, J$_{P-P}$=11.6, J$_{Pt-P}$=1491, trans to C), 19.2 (d, J$_{P-P}$=11.6, J$_{Pt-P}$=4536, trans to O).

3) Elemental analysis Calculated C: 65.31, H: 3.87 Found C: 64.88, H: 3.96.

(2) Preparation of Platinum-Containing Catalyst

The procedure of Example 1 was repeated except that using the optically active bisphosphine-aryloxyacyl platinum(II) complex (B) obtained above. The procedure in the NMR sample tube was repeated in the same manner as described in Example 1 to give a reaction mixture.

The reaction mixture was subjected to $^{31}$P-NMR analysis. The obtained $^{31}$P-NMR spectrum showed one signal of chemical shift(δ)=3.25 ppm (singlet) and a phosphorus—platinum coupling constant (J$_{Pt-P}$) of 3680 Hz.

(3) Preparation of β-Hydroxyester Derivative

The reaction of Example 1 was repeated except for using the reaction mixture obtained above and changing the reaction time to 170 hours, to give 148 mg of a colorless oily product (methyl 2,2-dimethyl-5-phenyl-3-trimethylsiloxypentanoate). Yield: 96%. The enantiomer excess determined in the same manner as in Example 1 was 91% e.e.

EXAMPLE 9
Preparation of β-Hydroxyester Derivative

The reaction of Example 1 was repeated using the platinum-containing catalyst solution obtained in Example 8, except for replacing the aldehyde with 3-methylbutanal (0.5 mmol.) and changing the reaction time to 144 hours, to give 129 mg of a colorless oily product (methyl 2,2,5-trimethyl-3-trimethylsiloxyhexanoate). Yield: 99%. The enantiomer excess determined in the same manner as in Example 5 was 88% e.e.

EXAMPLE 10
Preparation of β-Hydroxyester Derivative

The reaction of Example 1 was repeated using the platinum-containing catalyst solution obtained in Example 8, except for replacing the aldehyde with 3,3-dimethylbutanal (0.5 mmol.), to give 86 mg of a colorless oily product (methyl 2,2,5,5-tetramethyl-3-trimethylsiloxyhexanoate). Yield: 62%. The enantiomer excess determined in the same manner as in Example 5 was 62% e.e.

EXAMPLE 11
Preparation of β-Hydroxyester Derivative

The reaction of Example 1 was repeated using the platinum-containing catalyst solution obtained in Example 8, except for replacing the aldehyde with benzaldehyde (0.5 mmol.) and changing the reaction time to 19 hours, to give 138 mg of a colorless oily product (methyl 2,2-dimethyl-3-phenyl-3-trimethylsiloxypropanoate). Yield: 99%. The enantiomer excess determined in the same manner as in Example 5 was 56% e.e.

EXAMPLE 12

Preparation of β-Hydroxyester Derivative

The reaction of Example 1 was repeated using the platinum-containing catalyst solution obtained in Example 8, except for replacing the aldehyde with trans-cinnumaldehyde (0.5 mmol.) and changing the reaction time to 143 hours, to give 138 mg of a colorless oily product (methyl (E)-2,2-dimethyl-5-phenyl-3-trimethylsiloxypentanoate). Yield: 92%. The enantiomer excess determined in the same manner as in Example 5 was 46% e.e.

EXAMPLE 13

(1) Preparation of Optically Active Bisphosphine-Aryloxyacyl Platinum(II) Complex (C)

The procedure of Example 1 was repeated except for replacing the (R)-BINAP with (R)-Tol-BINAP (1.6 mmol.), to give 1.5 g of the aforementioned optically active bisphosphine-aryloxyacyl platinum(II) complex (C). Yield: 85%. The analytical data are given below.

1) $^1$H-NMR (400 MHz, CDCl$_3$) δ: 7.79–7.71 (m, 4H), 7.53 (d, J=8.3, 1H), 7.47–7.17 (m, 15H), 7.09–7.00 (m, 4H), 6.71 (dd, J=8.8, 8.8, 2H), 6.36 (d, J=7.8, 4H), 2.39 (s, 3H), 2.35 (s, 3H), 1.95 (s, 3H), 1.94 (s, 3H), 1.20 (s, 9H), 1.01 (s, 9H).

2) $^{31}$P{$^1$H}-NMR (160 MHZ, CDCl$_3$) δ: 21.8 (d, $J_{P-P}$=10.4, $J_{Pt-P}$=1517, trans to C), 18.6 (d, $J_{P-P}$=10.4, $J_{Pt-P}$=4455, trans to O).

3) Elemental analysis

Calculated C: 68.40, H: 5.47

Found C: 67.70, H: 5.35.

(2) Preparation of Platinum-Containing Catalyst

The procedure of Example 1 was repeated except that using the optically active bisphosphine-aryloxyacyl platinum(II) complex (C) obtained above. The procedure in the NMR sample tube was repeated in the same manner as described in Example 1 to give a reaction mixture.

The reaction mixture was subjected to $^{31}$P-NMR analysis. The obtained $^{31}$P-NMR spectrum showed one signal of chemical shift(δ)=1.93 ppm (singlet) and a phosphorus—platinum coupling constant ($J_{Pt-P}$) of 3682 Hz.

(3) Preparation of β-Hydroxyester Derivative

The reaction of Example 5 was repeated except for using the reaction mixture obtained above and changing the reaction time to 17.5 hours, to give 135 mg of a colorless oily product (methyl 2,2-dimethyl-3-phenyl-3-trimethylsiloxypropanoate). Yield: 97%. The enantiomer excess determined in the same manner as in Example 1 was 26% e.e.

EXAMPLE 14

(1) Preparation of Optically Active Bisphosphine-Aryloxyacyl Platinum(II) Complex (D)

The procedure of Example 1 was repeated except for replacing the (R)-BINAP with (R,R)-Me-DUPHOS (1.6 mmol.), to give 0.91 g of the aforementioned optically active bisphosphine-aryloxyacyl platinum(II) complex (D). Yield: 85%. The analytical data are given below.

1) $^1$H-NMR (400 MHz, CDCl$_3$) δ: 7.68–7.66 (m, 2H), 7.56–7.54 (m, 2H) 7.30 (d, J=7.8, 1H), 7.18 (dd, J=8.3, 7.8, 1H), 6.91 (d, J=8.3, 1H), 6.45 (dd, J=7.8, 7.8, 1H), 3.55–3.25 (m, 1H), 3.00–2.78 (m, 2H), 2.60–2.20 (m, 5H), 2.00–1.60 (m, 4H), 1.49 (dd, J=19.5, 6.8, 3H), 1.27 (dd, J=16.6, 6.4, 3H), 0.85 (dd, J=14.7, 7.3, 3H), 0.84 (dd, J=16.6, 7.3, 3H).

2) $^{31}$P{$^1$H}-NMR (160 MHZ, CDCl$_3$) δ: 66.0 (d, $J_{P-P}$=4.6, $J_{Pt-P}$=1530, trans to C), 52.7 (d, $J_{P-P}$=4.6, $J_{Pt-P}$=3935, trans to O).

3) Elemental analysis

Calculated C: 48.31, H: 5.19

Found C: 47.47, H: 5.10.

(2) Preparation of Platinum-Containing Catalyst

The procedure of Example 1 was repeated except that using the optically active bisphosphine-aryloxyacyl platinum(II) complex (D) obtained above. The procedure in the NMR sample tube was repeated in the same manner as described in Example 1 to give a reaction mixture.

The reaction mixture was subjected to $^{31}$P-NMR analysis. The obtained $^{31}$P-NMR spectrum showed one signal of chemical shift(δ)=60.7 ppm (singlet) and a phosphorus—platinum coupling constant ($J_{Pt-P}$) of 3488 Hz.

(3) Preparation of β-Hydroxyester Derivative

The reaction of Example 5 was repeated except for using the reaction mixture obtained above and changing the reaction time to 20.5 hours, to give 138 mg of a colorless oily product (methyl 2,2-dimethyl-3-phenyl-3-trimethylsiloxypropanoate). Yield: 99%. The enantiomer excess determined in the same manner as in Example 1 was 41% e.e.

EXAMPLE 15

(1) Preparation of Optically Active Bisphosphine-Aryloxyacyl Platinum(II) Complex (E)

The procedure of Example 1 was repeated except for replacing the (R)-BINAP with (R,R)-CHIRAPHOS (1.6 mmol.), to give 1.12 g of the aforementioned optically active bisphosphine-aryloxyacyl platinum(II) complex (E). Yield: 95%. The analytical data are given below.

1) $^1$H-NMR (400 MHz, CDCl$_3$) δ: 7.95–7.75 (m, 8H), 7.52–7.35 (m, 12H) 7.12 (d, J=7.8, 1H), 7.08 (dd, J=7.8, 7.8, 1H), 6.81 (d, J=8.3, 1H), 6.34 (dd, J=8.3, 7.8, 1H), 2.45–2.32 (m, 1H), 2.30–2.15 (m, 1H), 1.02 (dd, J=11.2, 6.8, 3H), 0.97 (dd, J=13.2, 6.8, 3H).

2) $^{31}$P{$^1$H}-NMR (160 MHZ, CDCl$_3$) δ: 45.7 (s, $J_{Pt-P}$=1482, trans to C), 35.9 (s, $J_{Pt-P}$=4162, trans to O).

3) Elemental analysis

Calculated C: 56.68, H: 4.35

Found C: 55.79, H: 4.19.

(2) Preparation of Platinum-Containing Catalyst

The procedure of Example 1 was repeated except that using the optically active bisphosphine-aryloxyacyl platinum(II) complex (E) obtained above. The procedure in the NMR sample tube was repeated in the same manner as described in Example 1 to give a reaction mixture.

The reaction mixture was subjected to $^{31}$P-NMR analysis. The obtained $^{31}$P-NMR spectrum showed one signal of chemical shift(δ)=45.2 ppm (singlet) and a phosphorus—platinum coupling constant ($J_{Pt-P}$) of 2960 Hz.

What is claimed is:

1. In a process for preparing an optically active β-hydroxyester derivative having the formula (1):

$$R^{13}-\underset{\underset{\underset{R^{20}}{|}}{\overset{\overset{R^{15}}{|}}{C}}-\overset{R^{16}}{\underset{|}{C}}-CO_2R^{17}}{O-Si-R^{18}}$$

(1)

wherein $R^{13}$ stands for an alkenyl group, an alkadienyl group, an alkynyl group, an aryl group, or a group represented by —CH$_2$R$^{14}$ in which R$^{14}$ is an alkyl group, an alkenyl group, an alkadienyl group, an alkynyl group, an aryl group, an aralkyl group, an alkoxyalkyl group or an aryloxyalkyl group, in which any of $R^{13}$ and $^{14}$ may have one or more substituent groups, and each of $R^{15}$, $R^{16}$, $R^{18}$, $R^{19}$ and $R^{20}$ independently stands for a hydrogen atom, a halogen atom, an alkyl group, an aryl group, an aralkyl group, an alkoxy group, an alkoxyalkyl group, an aryloxy group, or an aryloxyalkyl group; and $R^{17}$ stands for an alkyl group, an aryl group, or aralkyl group; provided that two groups selected from the group consisting of $R^{15}$ $R^{16}$ and $R^{17}$ may form a ring in conjunction with the adjacent atom or atoms, by enantioselective aldol addition reaction between an aldehyde having the formula (2) and a ketene silylacetal having the formula (3):

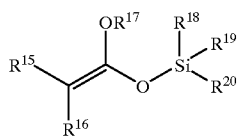

(3)

wherein each of $R^{13}$, $R^{15}$, $R^{16}$, $R^{17}$, $R^{18}$, $R^{19}$ and $R^{20}$ has the same meaning as above, the improvement which comprises performing the enantioselective aldol addition reaction in the presence of an organic base and a platinum-containing catalyst comprising an optically active bisphosphine-platinum complex having two P—Pt bondings which are equivalent to each other.

2. The process of claim 1, wherein the platinum-containing catalyst shows in its $^{31}$P NMR spectrum a single peak assigned to P—Pt bonding.

3. The process of claim 1, wherein the platinum-containing catalyst has been produced by treating an optically active bisphosphine-aryloxyacyl platinum(II) complex having the formula (4):

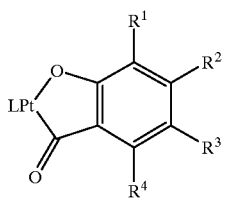

(4)

wherein each of $R^1$, $R^2$, $R^3$ and $R^4$ independently stands for a hydrogen atom, a halogen atom, an alkyl group, an alkenyl group, an aryl group, an aralkyl group, an alkoxy group, an aryloxy group, a nitro group, a cyano group or a dialkylamino group, provided that two groups selected from the group consisting of $R^1$, $R^2$, $R^3$ and $R^4$ may form a ring in conjunction with the adjacent atoms; and L stands for an optically active bisphosphine, with a non-coordinating or weakly coordinating super-strong acid in an oxygen-containing gas.

4. The process of claim 3, wherein the super-strong acid is selected from the group consisting of trifluoromethanesulfonic acid, tetrafluoroboric acid, hexafluorophosphoric acid, hexafluoroantimonic acid and perchloric acid.

5. The process of claim 1, wherein the optically-active bisphosphine has one of the following formulas:

(2-a)

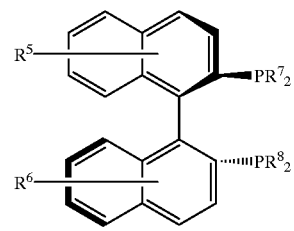

(2-b)

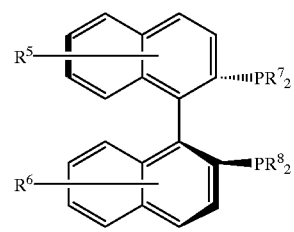

(3-a)

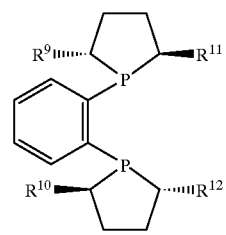

(3-b)

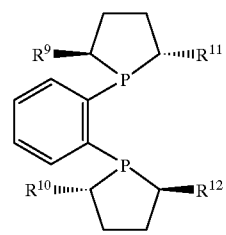

(4-a)

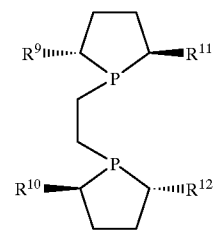

(4-b)

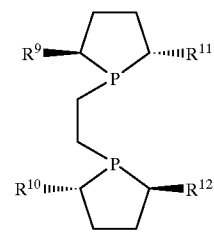

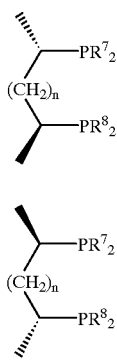

(5-a)

(5-b)

wherein each of $R^7$, $R^8$, $R^9$, $R^{10}$, $R^{11}$ and $R^{12}$ independently is an alkyl group, a cycloalkyl group, an aryl group, or an aralkyl group; each of $R^5$ and $R^6$ is a substituent group placed on the naphthalene ring, which independently is a halogen atom, an alkyl group, an aryl group or an aralkyl group; and n is an integer of 0 to 10.

6. The process of claim 1, wherein the platinum-containing catalyst has the formula (5):

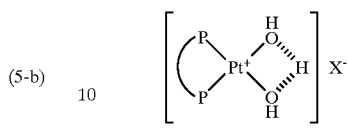

(5)

wherein the curve having P on either end represents an optically active bisphosphine, and $X^-$ is an anion.

7. The process of claim 1, wherein the organic base pyridine or a pyridine derivative having one or more substituents selected from the group consisting of an alkyl group, an alkenyl group, an aryl group, an aralkyl group, an alkoxy group, an aryloxy group, a dialkylamino group, a nitro group, and a halogen atom.

* * * * *